United States Patent [19]
Stendahl et al.

[11] Patent Number: 5,891,172
[45] Date of Patent: Apr. 6, 1999

[54] HIGH VOLTAGE PHASE SELECTOR SWITCH FOR EXTERNAL DEFIBRILLATORS

[75] Inventors: Gary B. Stendahl, Crystal; James E. Brewer, St. Paul, both of Minn.

[73] Assignee: SurVivaLink Corporation, Minneapolis, Minn.

[21] Appl. No.: 673,195

[22] Filed: Jun. 27, 1996

[51] Int. Cl.⁶ ........................................... A61N 1/39
[52] U.S. Cl. ................................................ 607/5; 607/74
[58] Field of Search ........................................ 607/5, 74

[56] References Cited

U.S. PATENT DOCUMENTS

| | | |
|---|---|---|
| 3,857,398 | 12/1974 | Rubin . |
| 3,886,950 | 6/1975 | Ukkestad et al. ............................ 607/5 |
| 4,504,773 | 3/1985 | Suzuki et al. ............................... 607/5 |
| 4,610,254 | 9/1986 | Morgan et al. . |
| 4,619,265 | 10/1986 | Morgan et al. . |
| 4,800,883 | 1/1989 | Winstrom ..................................... 607/5 |
| 4,823,796 | 4/1989 | Benson . |
| 5,097,830 | 3/1992 | Eikefjord et al. . |
| 5,199,429 | 4/1993 | Kroll et al. .................................. 607/5 |
| 5,230,336 | 7/1993 | Fain et al. .................................... 607/7 |
| 5,334,219 | 8/1994 | Kroll ............................................ 607/5 |
| 5,395,395 | 3/1995 | Hedberg ...................................... 607/5 |
| 5,405,361 | 4/1995 | Persson . |
| 5,411,525 | 5/1995 | Swanson et al. ............................ 607/5 |
| 5,425,749 | 6/1995 | Adams ......................................... 607/5 |
| 5,507,781 | 4/1996 | Kroll et al. .................................. 607/5 |
| 5,527,346 | 6/1996 | Kroll ............................................ 607/5 |
| 5,584,865 | 12/1996 | Hirschberg et al. ......................... 607/5 |
| 5,607,454 | 3/1997 | Cameron et al. ........................... 607/5 |
| 5,620,465 | 4/1997 | Olson et al. ................................. 607/5 |
| 5,620,470 | 4/1997 | Gliner et al. ................................ 607/5 |
| 5,634,938 | 6/1997 | Swanson et al. ........................... 607/5 |

FOREIGN PATENT DOCUMENTS

WO 95/05215  2/1995  WIPO .

OTHER PUBLICATIONS

W.A., Tacker, Jr., "Defibrillation of the Heart", Chapter 10, pp. 196–222, 1994.

*Primary Examiner*—William E. Kamm
*Assistant Examiner*—Kennedy J. Schaetzle
*Attorney, Agent, or Firm*—Patterson & Keough, P.A.

[57] ABSTRACT

Apparatus and method for selecting from a pair of capacitor banks for delivery of positive and negative polarity portions of a biphasic defibrillator pulse with a selector switch circuit for each capacitor bank, the circuit including a solid state phase selector switch preferably made up of a series connected plurality of IGBT's and each phase selector switch having a phase selector driver and select phase control for turning the phase selector switch ON and OFF when desired to start and truncate selected portions of the biphasic defibrillation pulse.

41 Claims, 5 Drawing Sheets

HIGH VOLTAGE PHASE SELECTOR SWITCH FOR EXTERNAL DEFIBRILLATORS

RELATED APPLICATIONS

The present invention is related to the following U.S. patent applications, all of which are assigned to the assignee of the present invention and all of which are hereby incorporated by reference: Parallel Charging of Mixed Capacitors, filed on even date herewith, Ser. No. 08/673,804; Biphasic Defibrillation Isolation Circuit, filed on even date herewith, U.S. Pat. No. 5,674,266; Fast Isolated IGBT Driver for High Voltage Switching Circuit, filed on even date herewith, Ser. No. 60/021,970, now abandoned; and High Voltage Series Diode Circuit for Capacitor Charging, filed on even date herewith, Ser. No. 08/881,210.

BACKGROUND OF THE INVENTION

1. Field of the Invention

This invention relates to the field of external defibrillators. In particular, the present invention relates to a high voltage phase selector switch for providing biphasic defibrillation pulses to a patient.

2. Description of the Related Art

Cardiac arrest, exposure to high voltage power lines and other trauma to the body can result in heart fibrillation which is the rapid and uncoordinated contraction of the cardiac muscle. The use of external defibrillators to restore the heartbeat to its normal pace through the application of an electrical shock is a well recognized and important tool for resuscitating patients. External defibrillation is typically used in emergency settings in which the patient is either unconscious or otherwise unable to communicate. Time is of the essence since studies have shown that the chances for successful resuscitation diminish approximately ten percent per minute.

Commercially available defibrillators such as those available from SurvivaLink Corporation, the assignee of the present application, are currently configured to produce monophasic waveform defibrillation pulses. Monophasic (i.e., single polarity) pulses such as a damped sine waveform and a truncated exponential waveform have been demonstrated to be effective for defibrillation, and meet standards promulgated by the Association for Advancement of Medical Instrumentation (AAMI). Electrical circuits for producing monophasic waveform defibrillation pulses are generally known and disclosed, for example, in the Persson U.S. Pat. No. 5,405,316 which is assigned to the assignee of the present invention and the disclosure of which is herein incorporated by reference.

The efficacy of biphasic waveform pulses (effectively two successive pulses of opposite polarities) has been established for implantable defibrillators. For example, studies conducted on implantable defibrillators have shown that biphasic waveform defibrillation pulses result in a lower defibrillation threshold than monophasic pulses. A variety of theories have been proposed to explain the defibrillation characteristics of biphasic waveform pulses but no definite conclusions have been reached.

It is anticipated that the efficacy and advantages of biphasic waveform pulses that have been demonstrated in implantable defibrillators will be demonstrated in external defibrillators as well. It has been known to use electromechanical vacuum or gas filled relays to switch the output of storage devices to form biphasic waveforms. These devices are electrically suitable for use in external defibrillators, but pose practical problems in that they are generally fragile, large and very expensive. One important shortcoming is that such devices are not suitable for breaking or interrupting large voltages and currents and, when called upon to do so, often damage the relay contacts. External defibrillators output defibrillation pulses in the range of 2000–3000 volts. The typical load for external defibrillators are in the range of approximately 25–225 ohms. At these voltages and resistances, the circuits must be able to handle currents in excess of 100 amps. This shortcoming is particularly significant when it is desired to truncate a first portion of a biphasic defibrillation pulse. In such circumstances, to truncate the pulse or waveform without damage to the contacts, it is known to short-circuit the capacitor bank supplying the pulse to be terminated or truncated. Such an approach suffers from the further shortcoming that the energy short-circuited is lost to the system, increasing inefficiency and adding electrical (and mechanical) stress to the components carrying short-circuit current. Thus, there is a continued need for a low cost, compact, and rugged switching circuit.

SUMMARY OF THE INVENTION

The present invention provides a low cost, compact and rugged external defibrillator having a high voltage and current switching circuit for delivering biphasic waveform defibrillation pulses. In the preferred embodiment of the present invention, the high voltage circuit includes first and second output terminals configured for electrical interconnection to electrodes, a supply terminal configured for electrical interconnection to a charge voltage potential, and two capacitor banks for storing electrical energy, with one bank used for the first (positive polarity) portion and the other bank for a second (negative polarity) portion of a biphasic defibrillation pulse. A pair of solid state charge switches are provided and are individually operable and responsive to charge control signals from a pair of charge control circuits to selectively electrically connect each of the capacitor banks to the pulse generator to charge the capacitor banks to a desired charge voltage potential.

Each of a pair of solid state selector circuits are connected to and individually responsive to respective selector driver circuits to selectively electrically connect one of the capacitor banks to output circuitry for providing one portion of the biphasic defibrillation pulse. Each of the driver circuits is responsive to a respective selector control circuit to control the state of the selector circuit to which it is connected. Each selector circuit preferably includes a pair of insulated gate bipolar transistors (IGBT's) connected in series and voltage balancing resistors connected in parallel therewith.

DETAILED DESCRIPTION OF THE INVENTION

The present invention will be described in detail below. In order to fully understand the present invention, a brief discussion of the associated circuitry for the external defibrillator will be given first.

Related Circuitry

Figure 1:
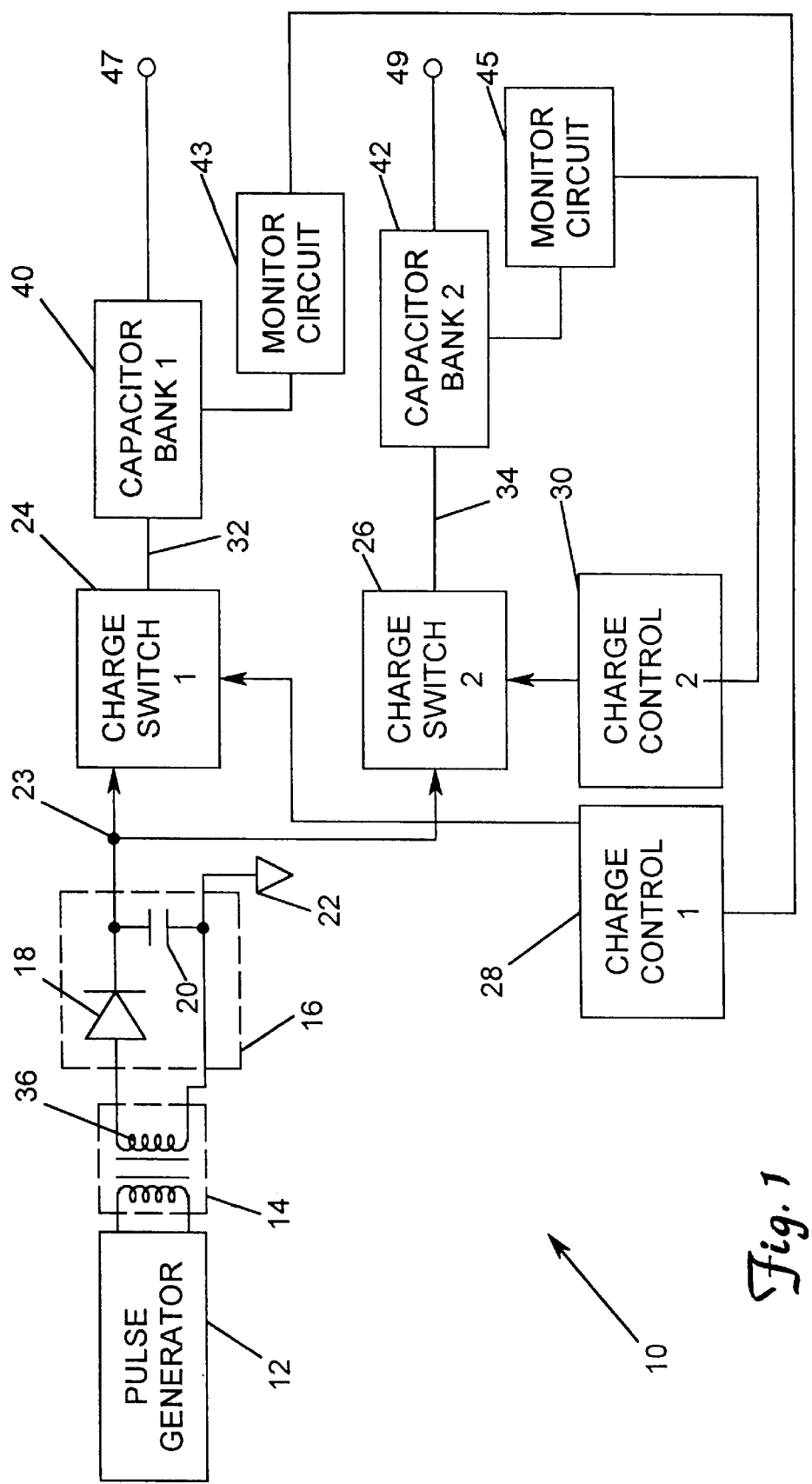
FIG. 1 is a block diagram of a capacitor charge control circuit in accordance with the present invention.

Referring now to FIG. 1, a charge control circuit 10 may be seen. Circuit 10 includes a pulse generator 12 connected to a pulse transformer 14 which is connected to a passive rectifying and filtering circuit 16. Circuit 16 is preferably made up of a high speed (fast recovery) diode 18, which is preferably a UF4007 type, available from General Instruments, and a capacitor 20 which may be in the range of 3–10 microfarads. Circuit common is indicated by an inverted triangle 22, and an output 23 of the rectifying and filtering circuit 16 is connected to first and second charge switches 24, 26. Charge switches 24, 26 are each preferably formed of one or more solid state switching devices such as a silicon controlled rectifier (SCR), a field effect transistor (FET), or an insulated gate bipolar transistor (IGBT). Such devices may be connected in series (to increase voltage capability) or in parallel (to increase current capability) as is well known in the art. Each of the charge switches 24, 26 is controlled by a separate one of a pair of charge control circuits 28, 30.

The respective outputs 32, 34 of the charge switches 24, 26 are individually connected to one of a pair of capacitor banks 40, 42. Output 32 is connected to a first capacitor bank 40, and output 34 is connected to a second capacitor bank 42. This portion of the circuitry will be described in detail with reference to a pair of capacitor banks but it should be noted that additional capacitor banks may also be included without departing from the spirit or scope of the invention. The output of capacitor bank 40 is connected to an electrode terminal 47 and the output of capacitor bank 42 is connected to an electrode terminal 49.

The circuit is designed to output to electrode terminals 47 and 49 a high voltage defibrillation pulse in the range of approximately 2000–3000 volts in the preferred embodiment. It should be noted however that greater or lesser discharge voltages can also be delivered without departing from the spirit or scope of the invention. In order to generate and deliver the voltage levels desired for defibrillation, a two step process is required. The first step is that of charging the capacitors. The second step is that of discharging the capacitors. To charge low cost, reliable capacitors rapidly to the desired voltage levels, the present invention utilizes charge control circuits 28, 30 and charge switch circuits 24, 26 to charge the capacitors in parallel. When connected in parallel, the total capacitance of a particular capacitance bank is the sum of all the capacitors connected in parallel, while the voltage across each of the individual capacitors is equal. To discharge the capacitors to electrode terminals 47, 49, charge control circuits 28, 30 and charge switch circuits 24, 26 configure the capacitors of a capacitor bank in series. This reduces the total capacitance to a fractional value of the individual capacitors and increase the voltage to the sum of the voltages across each individual capacitor.

The capacitor banks are preferably of differing capacitive values or differing voltage capacities. For example, in one embodiment, capacitor bank 40 has a total capacitance of 7200 microfarads while capacitor bank 42 has a total capacitance of 440 microfarads when connected in parallel for charging. Therefore, capacitor bank 42 will charge much more rapidly than will capacitor bank 40. During discharge, capacitor bank 40 has a total capacitance of 200 microfarads while capacitor bank 42 has a total capacitance of 110 microfarads while connected in series. It should be noted that many other capacitor banks could be utilized having many different capacitance values, or all having the same capacitance value without departing from the spirit or scope of the invention.

The operation of the charge control circuit 10 is as follows. Pulse generator 12 supplies a series, or train, of preferably square wave pulses, typically at a 50% duty cycle and having an amplitude of approximately 400 volts, at a frequency preferably between 5 KHz and 500 KHz. These pulses have a very rapid rise time. Since the fast rise times and high frequencies of the pulses cause avalanching of most common solid state devices of reasonable cost, the pulses are first passed through passive filter circuit 16. Diode 18 is a fast recovery diode that provides for charging of capacitor 20 and prevents discharge of the capacitor 20 through secondary 36 of pulse transformer 14. Capacitor 20 is preferably selected to be able to absorb and store the energy from at least one charge pulse from pulse generator 12.

As stated above, use of a pulse train with a very rapid rise time on individual pulses is desired, but would lead to avalanche breakdown of standard switches if coupled directly thereto. This would cause the switches to lose control of charging, and may lock the switches on, causing the capacitors to be continually charged until they are destroyed. This consequent loss of charging control is unacceptable. Use of rectifying and filtering circuit 16 avoids such avalanche triggering of solid state switches 24, 26 by keeping high dV/dt values from reaching switches 24, 26, allowing ordinary solid state devices to be used for switches 24, 26.

Figure 2:
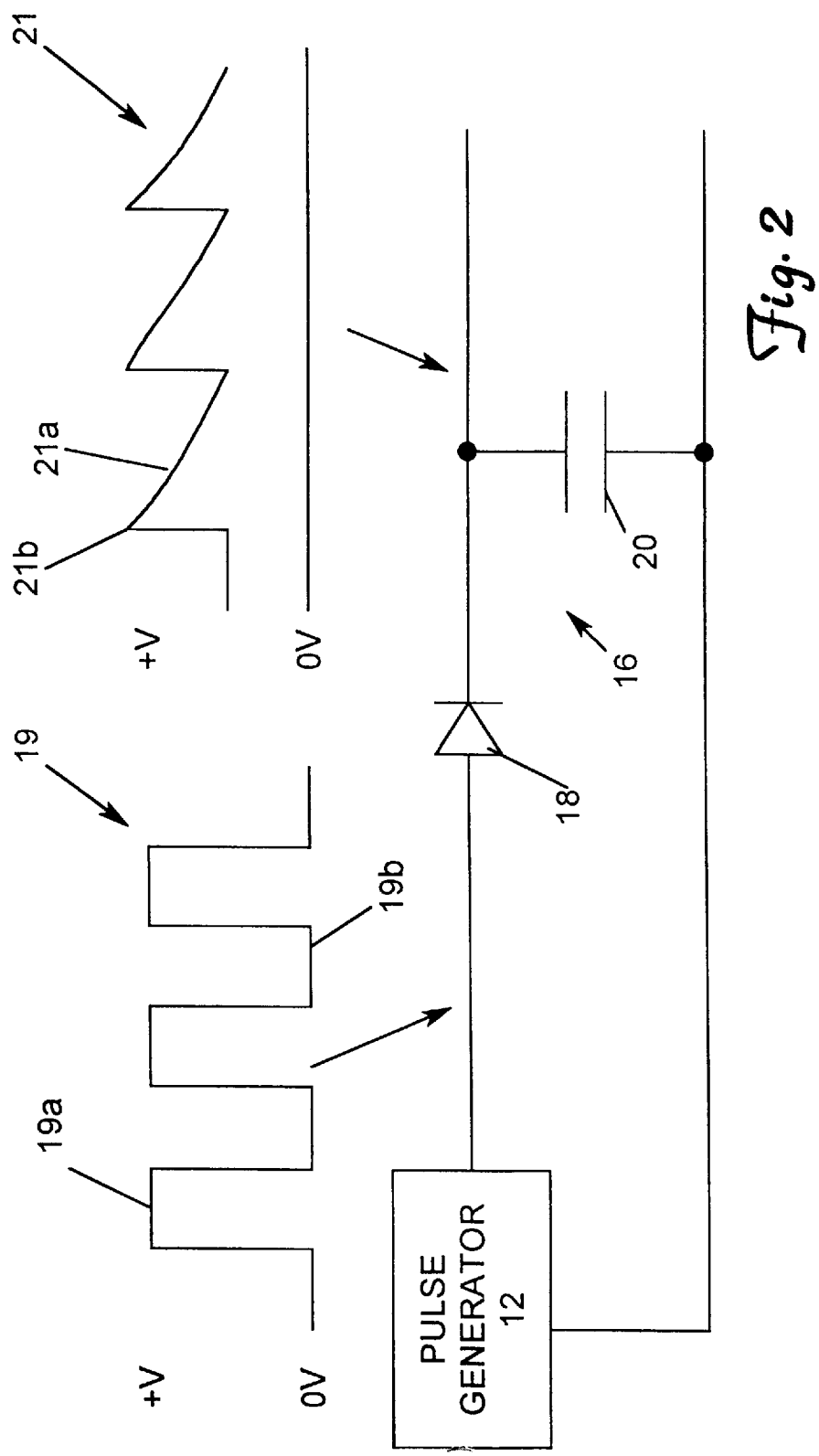
FIG. 2 illustrates a passive filter along with a pictorial representation of a signal before and after the filter.

FIG. 2 illustrates the passive filter along with a pictorial representation of a signal before and after the filter. As can be seen in waveform 19 illustrates the signal coming out of pulse generator 12. This signal is a series of square wave pulses having an amplitude of approximately 400 volts. After passing through filter 16, waveform 21 is obtained which is in the form of a DC level with a generally triangular ripple component. When the ON portion of waveform 19, illustrated at 19a, is seen at diode 18 the diode is forward biased allowing capacitor 20 to charge. Capacitor 20 is charged while diode 18 is forward biased. When signal 19 drops to zero, illustrated at 19b, diode 18 shuts off, halting the charging of capacitor 20. During the off period of diode 18 when the stored energy from capacitor 20 is transferred to the capacitor banks it's voltage drops slightly causing the triangular ripple voltage illustrated in waveform 21 at 21a. After capacitor 20 has a chance to discharge the energy stored therein, diode 18 turns back on due to the presence again of a positive voltage from pulse generator 12 causing waveform 21 to rise to a charged level, at 21b.

The DC charge on capacitor 20 is available to each of switches 24, 26 via lead 23 to be distributed to the capacitor banks as needed. It is to be understood that one or both of switches 24, 26 are on during charging. Both switches 24 and 26 may be on together or only one may be on, but at least one must be on during charging. When one or both of switches 24, 26 is on, the charge on capacitor 20 is coupled to the respective one or both of capacitor banks 40, 42.

As previously stated, the value of capacitor 20 is preferably chosen to be able to absorb and store the energy from one pulse. The energy stored in capacitor 20, which is now in the form of a DC level with a generally triangular ripple component, is available to be delivered to either capacitor bank via charge switches 24 or 26. It is also to be understood that the capacitor banks include slower acting diodes (illustrated as D1 et seq. in Figure 3 of U.S. Pat. No. 5,405,361, the disclosure of which is hereby incorporated by reference). Thus the pulse provided by transformer 14 is not instantly applied to the capacitors and the energy that is not immediately applied is stored in capacitor 20 and continues to be delivered between pulses from generator 12.

Figure 3:
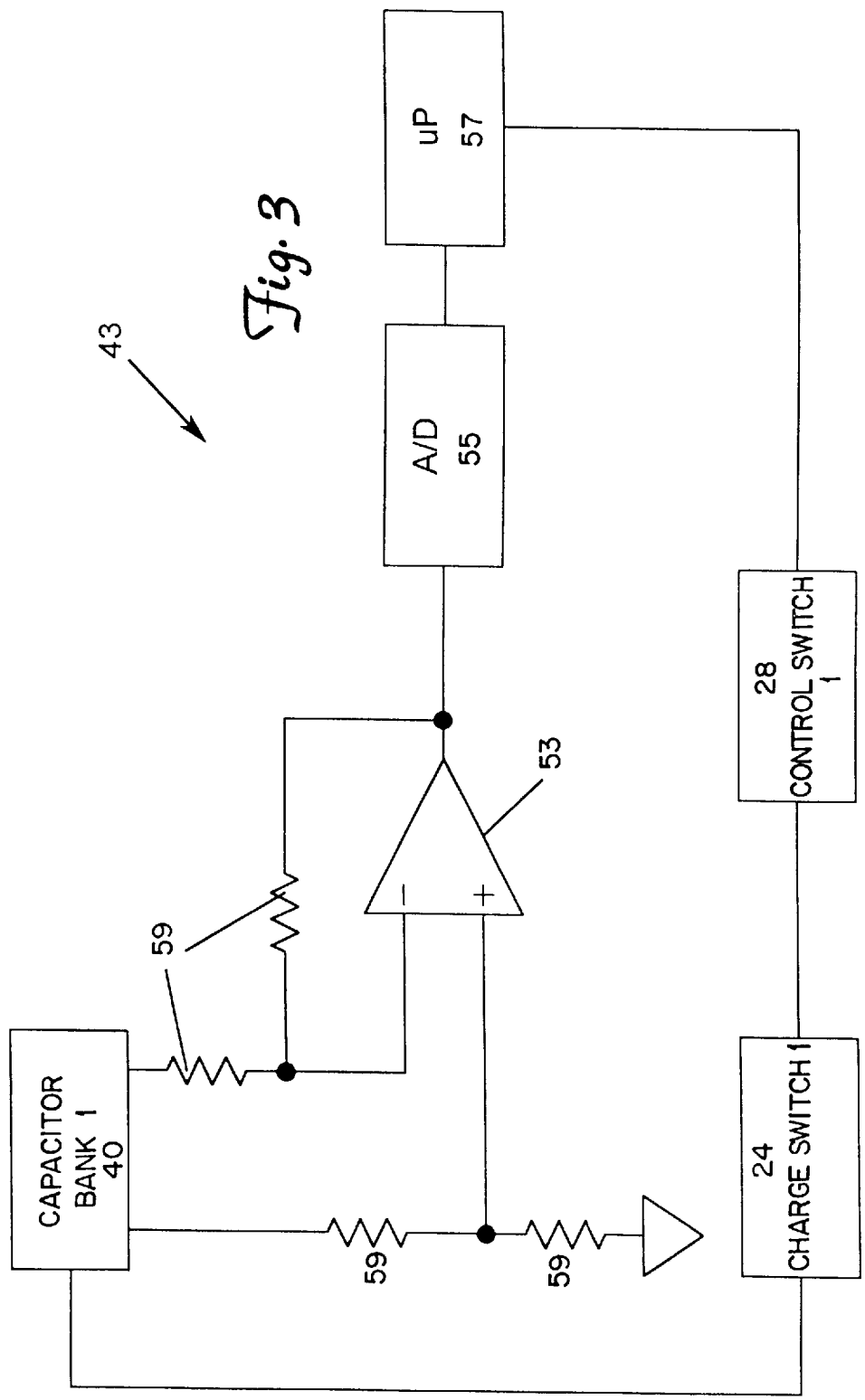
FIG. 3 illustrates one embodiment of a monitoring circuit of the circuit illustrated in FIG. 1.

Circuit 10 also includes voltage monitoring circuits 43, 45 for monitoring the voltage on capacitor banks 40 and 42, respectively. As can be seen in FIG. 1, monitor circuits 43 and 45 are connected to the respective capacitor banks and charge control circuit. Monitoring circuits 43 and 45 are illustrated schematically as block diagrams because there are many different embodiments of monitoring circuits that may be used without departing from the spirit or scope of the invention, such as analog circuitry, digital circuitry and solid state components, for example. FIG. 3 illustrates one preferred embodiment of monitoring circuit 43. It should be noted that monitoring circuit 45 is the same as monitoring circuit 43. As can be seen, an operational amplifier 53 is provided as is an analog to digital converter 55 and a microprocessor 57. Amplifier 53 is connected to capacitor bank 40 via a plurality of resistors 59. In operation, monitoring circuit 43 has a database of preset values stored in microprocessor 57. When capacitor bank 40 reaches the preset value selected in processor 57, charge control circuit 28 is instructed to halt the charging of capacitor bank 40. In an alternative embodiment, microprocessor 57 has the capability of computing an appropriate predetermined value for charging the respective capacitor bank.

When in the charging mode, one or a plurality of capacitor banks may be charged simultaneously. In the embodiment illustrated in FIG. 1 having first and second capacitor banks 40 and 42, if both capacitor banks 40 and 42 are being simultaneously charged, when capacitor bank 42 is fully charged, charge switch 26 is opened as a result of a command from monitoring circuit 45 and all of the charge available at capacitor 20 is then applied to capacitor bank 40 instead of splitting it between the two capacitor banks. When capacitor bank 40 is completely charged, charge switch 24 is opened as a result of a command from monitoring circuit 43. Capacitor banks 40 and 42 are now fully charged and the individual capacitors that make up a capacitor bank are ready to be switched into series for discharge.

DESCRIPTION OF THE PRESENT INVENTION

Figure 4:
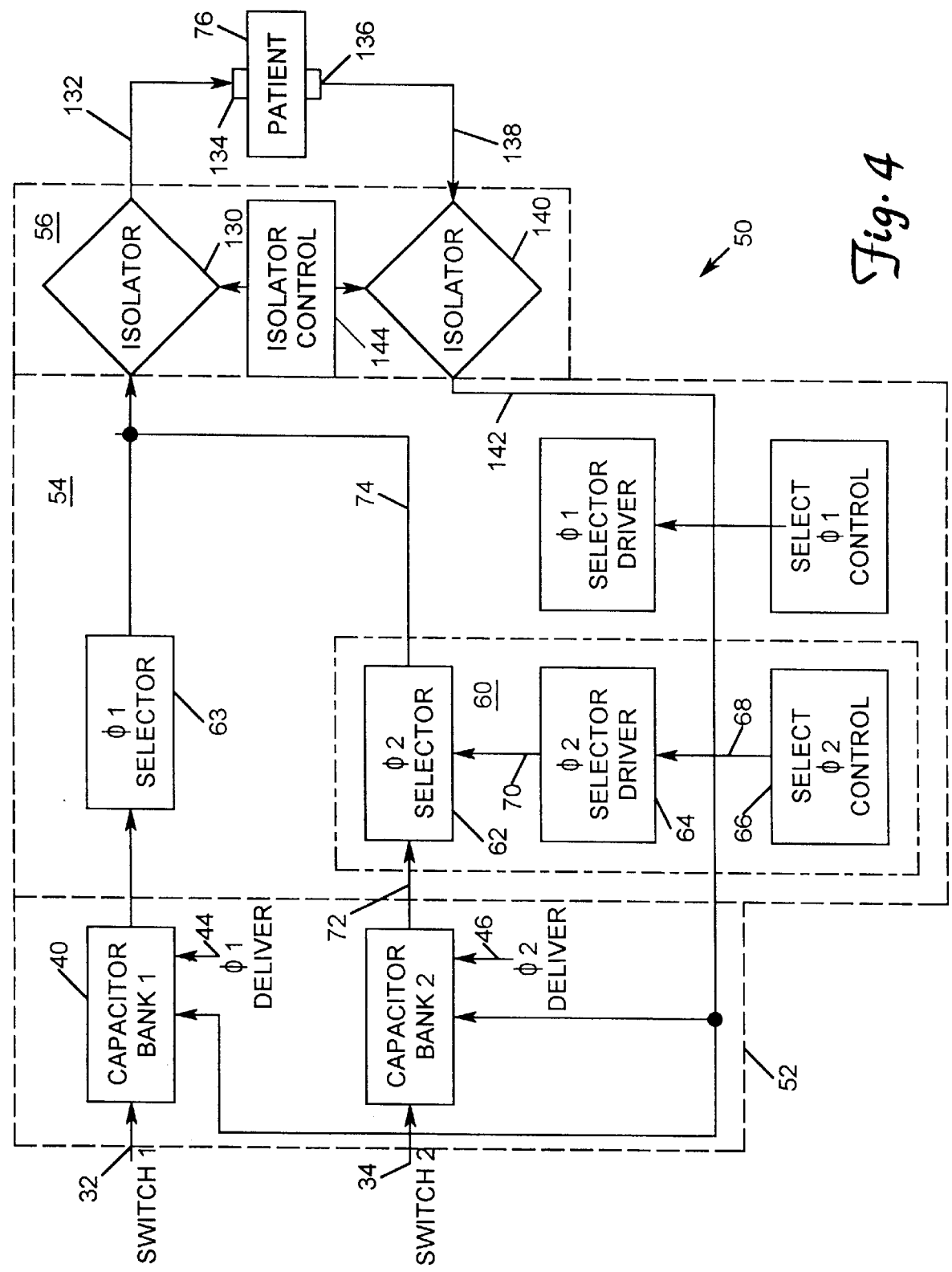
FIG. 4 is a block diagram of a capacitor bank selector and isolation subsystem useful in the practice of the present invention.

Referring now most particularly to FIG. 4, an output circuit 50 suitable for providing biphasic defibrillation pulses may be seen. Output circuit 50 includes a capacitor bank circuit 52, a selector circuit 54, and an isolator circuit 56. The capacitor bank circuit includes first and second capacitor banks 40, 42, each of which have respective phase delivery command lines 44, 46. In the preferred embodiment of the present invention, capacitor bank 40 is configured to discharge a positive first phase of the biphasic output pulse while capacitor bank 42 is configured to discharge a negative second phase. It should be noted that additional capacitor banks can be added without departing from the spirit or scope of the present invention. Selector circuit 54 has a pair of preferably identical selector subsystems. One subsystem 60 is indicated by a chain line. Subsystem 60 includes a solid state phase selector switch 62 connected to a phase selector driver 64 which in turn is connected to a select phase control 66. It is to be understood that select phase control 66 provides a signal on line 68 to activate and deactivate phase selector driver 64.

When phase selector driver 64 is activated, it drives phase selector switch 62 to a state of conduction (ON) between lines 72 and 74, connecting capacitor bank 42 to isolator circuit 56 and ultimately to a patient when isolator circuit is itself in a conducting state as will be described infra. When select phase control 66 deactivates phase select driver 64, phase selector switch 62 is rendered nonconductive (OFF) between lines 72 and 74, thus stopping any remainder of the portion of a biphasic defibrillation pulse from being delivered from the capacitor bank 42 to a patient 76. It is to be understood that the phase 1 selector subsystem (connected to capacitor bank 40) is formed of the same elements and operates identically to subsystem 60 in the embodiment shown in FIG. 4. To provide a monophasic defibrillation pulse, only the phase 1 selector subsystem is activated, since capacitor bank 40 is connected to provide a positive polarity output and capacitor bank 42 is connected to provide a negative polarity output.

When providing biphasic defibrillation pulse, it has been found preferable to proceed according to the following sequence:

1. Turn phase 1 selector switch ON, providing a first, positive polarity, exponentially decaying portion of the pulse.
2. Turn phase 1 selector switch OFF, truncating the first portion of the pulse at a desired point.
3. After a time delay, turn phase 2 selector switch ON, providing a second, negative polarity, exponentially decaying portion of the pulse.
4. Turn phase 2 selector switch OFF, truncating the second portion of the pulse at a desired point.

One important aspect of the present invention is the reduction of the transition time between phase 1 and phase 2. In known systems utilizing SCRs as switching mechanisms, any charge in the capacitors must be reduced below the level of the holding current for the SCR before a phase shift can occur. This can take up to 10 seconds due to the large amount of charge typically remaining on the capacitors. This is so even though photoflash capacitors are typically utilized due to their rapid discharge. In these known systems, SCR dump circuits are also required which are complicated circuits which require many components for each capacitor in the capacitor bank and which force the device to throw away all current stored in the bank.

In the present invention, the SCR's have been replaced by IGBT's and photoflash capacitors are no longer needed, allowing cheaper, mass-produced products to be used. The delay of switching between phase 1 and phase 2 depends only on the length of time to shut off phase 1 long enough to allow phase 2 to be energized. This time frame is on the order of microseconds. The discharge of current from either capacitor bank 40, 42 may be halted at any time and is able to do so when voltage levels are in excess of 2000–3000 volts. The discharge of an extremely high voltage phase of opposite polarity is begun within 2–3 microseconds following the truncation of the first phase.

Figure 5:
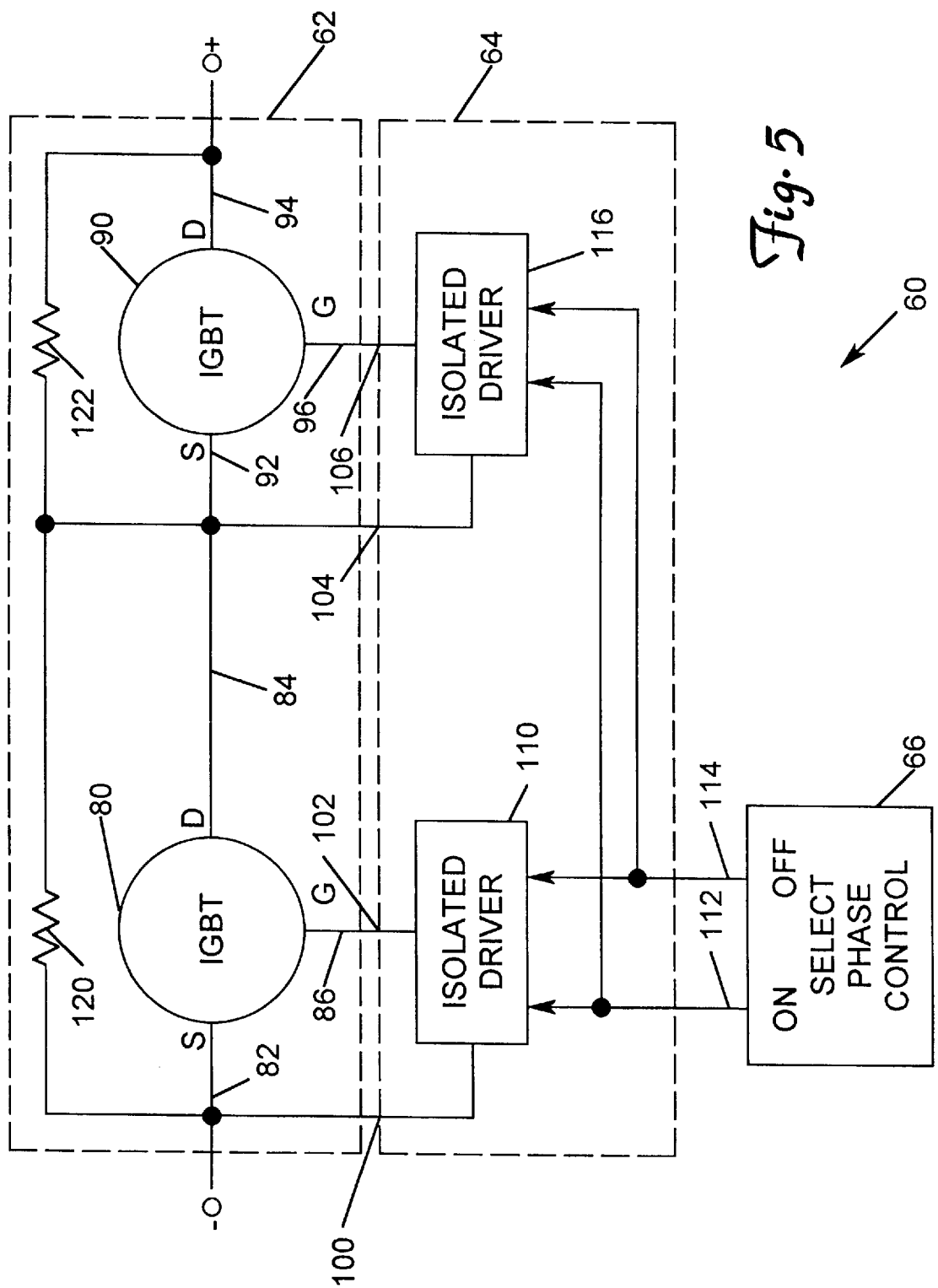
FIG. 5 is a more detailed block diagram of an individual selector, driver and control useful in the practice of the present invention.

Referring now also to FIG. 5, details of the phase selector switch 62 may be seen. The preferred embodiment will be described with reference to a pair of IGBT's, but it should be noted that more may be used as will be described below. To withstand the high voltages and high currents encountered in providing defibrillation pulses (whether monophasic or biphasic) two IGBT's are connected in series. As stated in the background section, extremely high voltage and current levels are present in external defibrillators. Voltage levels on the order of 2000–3000 volts and currents in excess of 100 amps are common. A first IGBT 80 has a power input 82 and a power output 84 and a signal input or gate 86.

Similarly, a second IGBT 90 also has a power input 92, a power output 94, and a signal input, or gate, 96. Referring now also to FIG. 4, power input 82 is connected to lead 72 carrying the output of capacitor bank 42. Power output 84 is connected to power input 92 and power output 94 is connected to lead 74. The connection 70 between phase selector driver 64 and phase selector switch 62 is actually made up of four connections 100, 102, 104, 106. Connections 100 and 102 couple an isolated driver 110 to IGBT 80. Similarly connection 68 between the select phase control 66 and the phase selector driver 64 actually includes two leads 112, 114. As is shown, driver 116 for IGBT 90 (and associated connections) is identical to that described in connection with driver 110. Each of IGBT's 80, 90 is preferably rated to deliver a 360 Joule pulse into a 25 ohm load [at pulse repetition rate of 1 per 5 seconds], and is also preferably rated to withstand 1200 volts in the OFF condition. One such IGBT is type is IXGH25N120A available from IXYS. To prevent unbalanced voltage between IGBT's 80, 90 in the OFF condition, resistors 120, 122 are connected in series with each other and in parallel as a voltage divider across the series connection of IGBT's 80, 90. The resistance of each resistor 120, 122 is preferably 3 mega ohms.

By adding additional IGBT's or by using IGBT's having higher current and voltage limits, the circuit can output each phase successfully at any current or voltage level. Specifically, the present invention allows the switching from phase 1 to phase 2 at voltage levels greater than 1000 volts. For example, by putting four 1200 volt IGBT's in series for each phase, the circuit can withstand (or hold off) 4800 volts per phase or a total of 9600 volts.

The operation of selector subsystem 60 is as follows. When it is desired to turn phase selector switch 62 ON, a low level signal is generated by select phase control 66, providing a logic ON signal on lead 112 and removing a logic OFF signal on lead 114. Drivers 110 and 116 may be any type of voltage isolating driver circuits sufficient to meet the speed and voltage requirements of the defibrillator system. Presently, magnetically isolated conventional driver circuits are preferred. When it is time to turn off phase 1, IGBT's 80 and 90 are closed thus halting the output to the patient without dumping the charge through an auxiliary SCR dumping circuit. The same is done for phase 2. During the time that the current flows through the IGBT's, peak currents are all within the safe operating areas.

Because dumping the charge in capacitor banks 40 and 42 is not needed to change phases, any dumping circuitry desired can be constructed from non-high speed components because time is not critical. This greatly reduces the cost of the components required.

The invention is not to be taken as limited to all of the details thereof as modifications and variations thereof may be made without departing from the spirit or scope of the invention.

What is claimed is:

1. An apparatus for delivering biphasic high voltage defibrillation pulses in an external defibrillator circuit comprising:
    a pulse generator;
    a pulse transformer having a primary winding connected to the pulse generator and having a secondary winding magnetically coupled to the primary winding;
    a first capacitor bank comprised of at least one capacitor and having a first polarity for producing a first phase of the biphasic defibrillation pulse; a second capacitor bank comprised of at least one capacitor and having a second polarity opposite the first polarity for producing a second phase of the biphasic defibrillation pulse;
    a first switch having an input connected to the secondary winding of the pulse transformer and an output connected to the first capacitor bank; a second switch having an input connected to the secondary winding of the pulse transformer and an output connected to the second capacitor bank;
    electrode terminals for delivering the high voltage defibrillation pulse to a patient;
    a third switch connected between the first capacitor bank and the electrode terminals for selectively providing and interrupting a path therebetween; and
    a fourth switch connected between the second capacitor bank and the electrode terminals for selectively providing and interrupting a path therebetween.

2. The apparatus as in claim 1 further comprising a first phase selector driver connected to the third switch and a second phase selector driver connected to the fourth switch.

3. The apparatus as in claim 2 further comprising a first select phase control circuit connected to the first phase selector driver and a second select phase control circuit connected to the second phase selector driver.

4. The apparatus of claim 1 wherein third and fourth switches comprise at least one insulated gate bipolar transistor.

5. The apparatus of claim 1 wherein the third and fourth switches comprise an isolated driver to selectively turn the switches ON and OFF.

6. The apparatus of claim 5 wherein the isolated driver further comprises a magnetically coupled gate driver circuit.

7. The apparatus of claim 1 wherein each of the third and fourth switches comprise a pair of insulated gate bipolar transistors connected in series.

8. The apparatus of claim 7 further comprising a pair of resistors connected in series with each other and wherein each resistor is connected in parallel with one of the pair of insulated gate bipolar transistors.

9. The apparatus of claim 8 wherein the resistance of each resistor is substantially the same as the resistance of the other resistor to balance the voltage across the pair of insulated gate bipolar transistors.

10. An improved external defibrillator for connection to a pair of electrodes, the improvement comprising a pair of separate, non-serially arranged, capacitor banks for delivering biphasic high voltage defibrillation pulses to the electrodes and a biphasic selector switch having a pair of solid state switching means wherein one of the pair of switching means is connected between one of the capacitor banks and the electrodes for selectively providing and interrupting a path therebetween and the other of the pair of switching means is connected between the other capacitor bank and the electrodes.

11. The apparatus of claim 10 wherein each of the solid state switch means comprises at least one insulated gate bipolar transistor.

12. The apparatus of claim 10 wherein each of the solid state switch means comprises an isolated driver to selectively turn the solid state switch ON and OFF.

13. The apparatus of claim 12 wherein the isolated driver further comprises a magnetically coupled gate driver circuit.

14. The apparatus of claim 13 wherein isolated driver further comprises a pulse transformer.

15. The apparatus of claim 10 wherein each of the solid state switch means comprises a pair of insulated gate bipolar transistors connected in series.

16. The apparatus of claim 15 further comprising a pair of high ohmic value resistors connected in series with each other and wherein each resistor is connected in parallel with one of the pair of insulated gate bipolar transistors.

17. The apparatus of claim 16 wherein the resistance of each resistor is substantially the same as the resistance of the other resistor to balance the voltage across the pair of insulated gate bipolar transistors.

18. A method of selectively coupling each of a pair of capacitor banks to a patient to provide biphasic defibrillation pulses, the method comprising the steps of:

a) arranging a first capacitor bank, having a first polarity, non-serially relative to a second capacitor bank, having a second polarity opposite the first polarity;

b) interposing a first solid state selector switch between the first capacitor bank and a patient;

c) interposing a second solid state selector switch between the second capacitor bank and the patient;

d) selectively turning the first solid state selector switch ON and the second solid state selector switch OFF to provide a first portion of a biphasic defibrillation pulse; and e) selectively turning the first solid state selector switch OFF and the second solid state selector switch ON to provide a second portion of the biphasic defibrillation pulse opposite in polarity from the first portion of the biphasic defibrillation pulse.

19. The method of claim 18 wherein each of steps c) and d) includes coupling a logic level signal to each of the first and second solid state selector switches to turn the switches ON in response to a select phase control command.

20. The method of claim 18 wherein each of steps c) and d) is carried out utilizing an insulated gate bipolar transistor in the solid state selector switch.

21. A method of providing a truncated defibrillation pulse from an external defibrillator comprising the steps of:

a) interposing only one solid state selector switch between a capacitor bank and a patient;

b) selectively turning the solid state selector switch ON to commence delivery of an exponentially decaying defibrillation pulse to the patient; and c) selectively turning the solid state selector switch OFF to truncate the exponential decay and stop delivery of the defibrillation pulse to the patient.

22. The method of claim 21 wherein step a) is carried out using an insulated gate bipolar transistor is used for the solid state selector switch.

23. An apparatus for delivering biphasic high voltage defibrillation pulses in an external defibrillator circuit comprising:

a pulse generator;

a pulse transformer having a primary winding connected to the pulse generator and having a secondary winding magnetically coupled to the primary winding;

a first capacitor bank comprised of at least one capacitor;

a second capacitor bank comprised of at least one capacitor;

a first switch having an input connected to the secondary winding of the pulse transformer and an output connected to the first capacitor bank;

a second switch having an input connected to the secondary winding of the pulse transformer and an output connected to the second capacitor bank;

electrode terminals for delivering the high voltage defibrillation pulse to a patient;

a third switch connected between the first capacitor bank and the electrode terminals for selectively providing and interrupting a path therebetween;

a fourth switch connected between the second capacitor bank and the electrode terminals for selectively providing and interrupting a path therebetween;

a first phase selector driver connected to the third switch; and a second phase selector driver connected to the fourth switch.

24. The apparatus as in claim 23 further comprising a first select phase control circuit connected to the first phase selector driver and a second select phase control circuit connected to the second phase selector driver.

25. An apparatus for delivering biphasic high voltage defibrillation pulses in an external defibrillator circuit comprising:

a pulse generator;

a pulse transformer having a primary winding connected to the pulse generator and having a secondary winding magnetically coupled to the primary winding;

a first capacitor bank comprised of at least one capacitor;

a second capacitor bank comprised of at least one capacitor;

a first switch having an input connected to the secondary winding of the pulse transformer and an output connected to the first capacitor bank;

a second switch having an input connected to the secondary winding of the pulse transformer and an output connected to the second capacitor bank;

electrode terminals for delivering the high voltage defibrillation pulse to a patient;

a third switch connected between the first capacitor bank and the electrode terminals for selectively providing and interrupting a path therebetween, the third switch comprising at least one insulated gate bipolar transistor; and a fourth switch connected between the second capacitor bank and the electrode terminals for selectively providing and interrupting a path therebetween, the fourth switch comprising at least one insulated gate bipolar transistor.

26. An apparatus for delivering biphasic high voltage defibrillation pulses in an external defibrillator circuit comprising:

a pulse generator;

a pulse transformer having a primary winding connected to the pulse generator and having a secondary winding magnetically coupled to the primary winding;

a first capacitor bank comprised of at least one capacitor;

a second capacitor bank comprised of at least one capacitor;

a first switch having an input connected to the secondary winding of the pulse transformer and an output connected to the first capacitor bank;

a second switch having an input connected to the secondary winding of the pulse transformer and an output connected to the second capacitor bank;

electrode terminals for delivering the high voltage defibrillation pulse to a patient;

a third switch connected between the first capacitor bank and the electrode terminals for selectively providing and interrupting a path therebetween, the third switch comprising a pair of insulated gate bipolar transistors connected in series; and a fourth switch connected between the second capacitor bank, the fourth switch comprising a pair of insulated gate bipolar transistors connected in series;

electrode terminals for selectively providing and interrupting a path therebetween.

27. The apparatus of claim 26 further comprising a pair of resistors connected in series with each other and wherein each resistor is connected in parallel with one of the pair of insulated gate bipolar transistors.

28. The apparatus of claim 27 wherein the resistance of each resistor is substantially the same as the resistance of the other resistor to balance the voltage across the pair of insulated gate bipolar transistors.

29. An apparatus for delivering biphasic high voltage defibrillation pulses in an external defibrillator circuit comprising:

a pulse generator;

a pulse transformer having a primary winding connected to the pulse generator and having a secondary winding magnetically coupled to the primary winding;

a first capacitor bank comprised of at least one capacitor;

a second capacitor bank comprised of at least one capacitor;

a first switch having an input connected to the secondary winding of the pulse transformer and an output connected to the first capacitor bank;

a second switch having an input connected to the secondary winding of the pulse transformer and an output connected to the second capacitor bank;

electrode terminals for delivering the high voltage defibrillation pulse to a patient;

a third switch connected between the first capacitor bank and the electrode terminals for selectively providing and interrupting a path therebetween, and configured and arranged to produce only one of at least one of a first phase and a second phase of the biphasic defibrillation pulse; and a fourth switch connected between the second capacitor bank and the electrode terminals for selectively providing and interrupting a path therebetween, and configured and arranged to produce only one of at least one of a first phase and a second phase of the biphasic defibrillation pulse.

30. An apparatus for delivering biphasic high voltage defibrillation pulses in an external defibrillator circuit comprising:

a pulse generator;

a pulse transformer having a primary winding connected to the pulse generator and having a secondary winding magnetically coupled to the primary winding;

a first capacitor bank comprised of at least one capacitor;

a second capacitor bank comprised of at least one capacitor;

a first switch having an input connected to the secondary winding of the pulse transformer and an output connected to the first capacitor bank;

a second switch having an input connected to the secondary winding of the pulse transformer and an output connected to the second capacitor bank;

electrode terminals for delivering the high voltage defibrillation pulse to a patient;

a third switch connected between the first capacitor bank and the electrode terminals for selectively providing and interrupting a path therebetween; and a fourth switch connected between the second capacitor bank and the electrode terminals for selectively providing and interrupting a path therebetween;

wherein an output of the third switch is connected to an output of the fourth switch.

31. An apparatus for delivering biphasic high voltage defibrillation pulses in an external defibrillator circuit comprising:

a pulse generator;

a pulse transformer having a primary winding connected to the pulse generator and having a secondary winding magnetically coupled to the primary winding;

a first capacitor bank comprised of at least one capacitor;

a second capacitor bank comprised of at least one capacitor and being isolated electrically from the first capacitor bank;

a first switch having an input connected to the secondary winding of the pulse transformer and an output connected to the first capacitor bank;

a second switch having an input connected to the secondary winding of the pulse transformer and an output connected to the second capacitor bank;

electrode terminals for delivering the high voltage defibrillation pulse to a patient;

a third switch connected between the first capacitor bank and the electrode terminals for selectively providing and interrupting a path therebetween; and a fourth switch connected between the second capacitor bank and the electrode terminals for selectively providing and interrupting a path therebetween.

32. An apparatus for delivering biphasic high voltage defibrillation pulses in an external defibrillator circuit comprising:

a pulse generator;

a pulse transformer having a primary winding connected to the pulse generator and having a secondary winding magnetically coupled to the primary winding;

a first capacitor bank comprised of at least one capacitor;

a second capacitor bank comprised of at least one capacitor;

a first switch having an input connected to the secondary winding of the pulse transformer and an output connected to the first capacitor bank;

a second switch having an input connected to the secondary winding of the pulse transformer and an output connected to the second capacitor bank;

electrode terminals for delivering the high voltage defibrillation pulse to a patient;

a third switch connected between the first capacitor bank and the electrode terminals for selectively providing and interrupting a path therebetween; and a fourth switch connected between the second capacitor bank and the electrode terminals for selectively providing and interrupting a path therebetween.

33. An improved external defibrillator, the improvement comprising a pair of separate capacitor banks for delivering biphasic high voltage defibrillation pulses to electrodes and a biphasic selector switch having a pair of solid state switching means wherein one of the pair of switching means is connected between one of the capacitor banks and the electrodes for selectively providing and interrupting a path therebetween and the other of the pair of switching means is connected between the other capacitor bank and the electrodes, wherein each of the solid state switch means comprises at least one insulated gate bipolar transistor.

34. An improved external defibrillator for connection to a pair of electrodes, the improvement comprising a pair of separate capacitor banks for delivering biphasic high voltage defibrillation pulses to electrodes and a biphasic selector switch having a pair of solid state switching means wherein one of the pair of switching means is connected between one of the capacitor banks and the electrodes for selectively providing and interrupting a path therebetween and the other of the pair of switching means is connected between the other capacitor bank and the electrodes, wherein each of the solid state switch means comprises an isolated driver to selectively turn the solid state switch ON and OFF.

35. The apparatus of claim 34 wherein the isolated driver further comprises a magnetically coupled gate driver circuit.

36. The apparatus of claim 35 wherein isolated driver further comprises a pulse transformer.

37. An improved external defibrillator for connection to a pair of electrodes, the improvement comprising a pair of separate capacitor banks for delivering biphasic high voltage defibrillation pulses to electrodes and a biphasic selector switch having a pair of solid state switching means wherein one of the pair of switching means is connected between one of the capacitor banks and the electrodes for selectively providing and interrupting a path therebetween and the other of the pair of switching means is connected between the other capacitor bank and the electrodes, wherein each of the solid state switch means comprises a pair of insulated gate bipolar transistors connected in series.

38. The apparatus of claim 37 further comprising a pair of high ohmic value resistors connected in series with each other and wherein each resistor is connected in parallel with one of the pair of insulated gate bipolar transistors.

39. The apparatus of claim 38 wherein the resistance of each resistor is substantially the same as the resistance of the other resistor to balance the voltage across the pair of insulated gate bipolar transistors.

40. A method of selectively coupling each of a pair of capacitor banks to a patient to provide biphasic defibrillation pulses, the method comprising the steps of:

a) interposing a first solid state selector switch, which includes a first insulated gate bipolar transistor, between a first capacitor bank and a patient;

b) interposing a second solid state selector switch, which includes a second insulated gate bipolar transistor, between a second capacitor bank and the patient;

c) selectively turning the first solid state selector switch ON and the second solid state selector switch OFF to provide a first portion of a biphasic defibrillation pulse; and d) selectively turning the first solid state selector switch OFF and the second solid state selector switch ON to provide a second portion of the biphasic defibrillation pulse opposite in polarity from the first portion of the biphasic defibrillation pulse.

41. The method of claim 40 wherein each of steps c) and d) is carried out using an insulated gate bipolar transistor in the solid state selector switch.

\* \* \* \* \*